United States Patent
Massi et al.

(10) Patent No.: US 6,383,157 B1
(45) Date of Patent: May 7, 2002

(54) WRIST-BAND FOR THE PREVENTION AND THE TREATMENT OF THE CARPAL TUNNEL SYNDROME AND ITS POSITIONING OPERATING MODE

(76) Inventors: Stefano Massi; Gabriele Massi, both of Piazza Liberta, 22, I-52027 San Giovanni Valdarno (IT)

(*) Notice: Subject to any disclaimer, the term of this patent is extended or adjusted under 35 U.S.C. 154(b) by 0 days.

(21) Appl. No.: 09/462,622
(22) PCT Filed: Jul. 9, 1998
(86) PCT No.: PCT/IT98/00193
  § 371 Date: Mar. 7, 2000
  § 102(e) Date: Mar. 7, 2000
(87) PCT Pub. No.: WO99/02111
  PCT Pub. Date: Jan. 21, 1999

(30) Foreign Application Priority Data

Jul. 7, 1997 (IT) .......................................... FI97A0164

(51) Int. Cl.[7] .................................................. A61F 5/00
(52) U.S. Cl. .......................... 602/21; 128/878; 128/879
(58) Field of Search .............................. 602/20, 21, 62; 128/877, 878, 879

(56) References Cited

U.S. PATENT DOCUMENTS

| 5,003,967 A | * | 4/1991 | McConnell | 602/21 |
| 5,076,289 A | * | 12/1991 | Darling | 128/877 |
| 5,649,900 A | * | 7/1997 | Kline | 602/21 |
| 6,119,267 A | * | 9/2000 | Pozzi | 602/21 |

* cited by examiner

Primary Examiner—Michael A. Brown
(74) Attorney, Agent, or Firm—Harrsion & Egbert

(57) ABSTRACT

A wrist-band for preventing and treating carpal tunnel syndrome by allowing limited movements of the wrist of the user according to the bending extension movements. The wrist band includes a multi-layer soft and flexible band which is suitable for being positioned on an a portion between the hand and the forearm corresponding to the carpiulnaris articulation of the user. The band includes five adjacent portions. A first portion is a terminal portion having three rounded sides connected together. A second portion is connected to the first portion and includes a superior rounded side and an inferior rectilinear side. A third portion is connected to the second portion and is suitable for overlapping the first portion. A fourth portion is connected to the third portion and is of a size smaller than the first, second and third portions. The fifth portion is a terminal tongue-shaped portion having a fastener thereon so as to secure the wrist band around the wrist of the user.

17 Claims, 1 Drawing Sheet

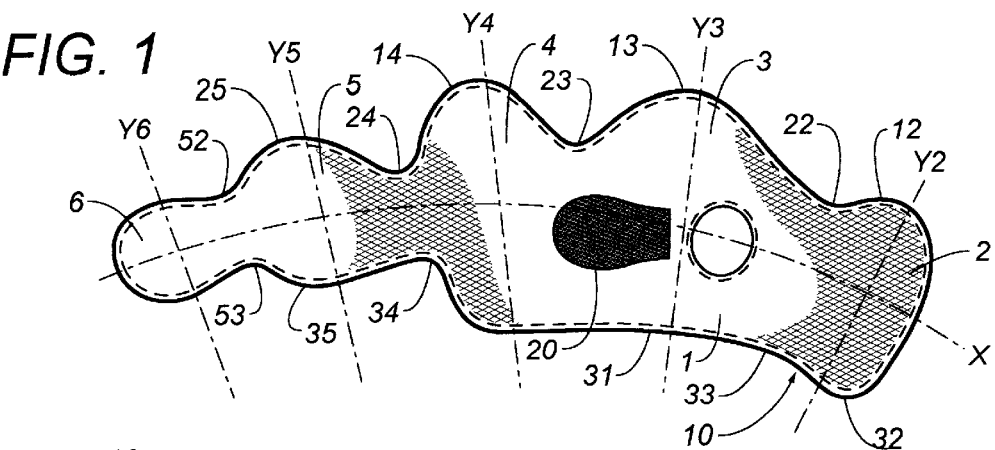
FIG. 1
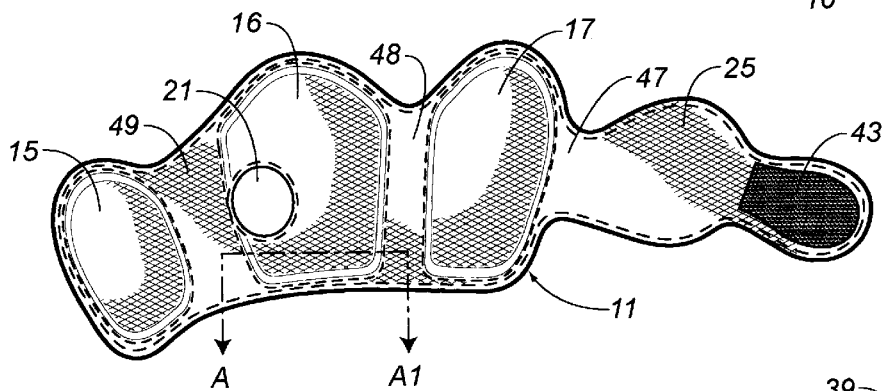
FIG. 2
FIG. 3
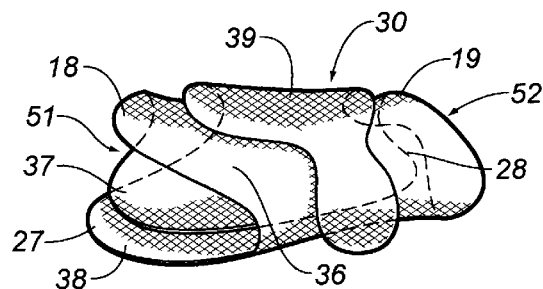
FIG. 4
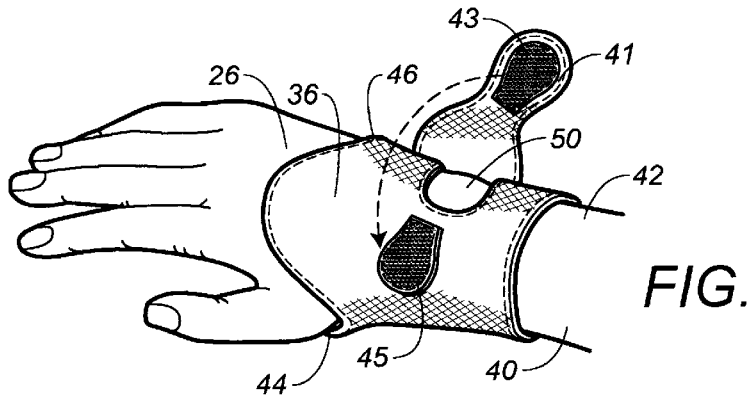
FIG. 5

WRIST-BAND FOR THE PREVENTION AND THE TREATMENT OF THE CARPAL TUNNEL SYNDROME AND ITS POSITIONING OPERATING MODE

BACKGROUND OF THE INVENTION

1. Field of the Invention

The present invention relates to orthopedic remedies. More particularly, the present invention relates to wrist bands as used for the prevention and treatment of carpal tunnel syndrome.

2. Description of Related Art

Problems of the wrist are currently well known that have symptoms due to factors such as it cervical arthrosis or to insufficient circulation. These problems are often submitted to specialized treatment at a late stage or are treated in an improper manner.

To better illustrate the problems associated with the wrist, the movements of the human wrist are described herein. The carpiradialis and carpimedian articulation movements are used to cause the positioning of the hand in relation to the forearm. These movements can be characterized as bending movements, extension movements, radial and cubital inclination movements, and circling and rotation movements. In order to accomplish the bending movement, the palmar face of the hand bends according to the front surface of the forearm. For an extension movement, the dorsal face of the hand bends according to a rear surface of the forearm. The cubital inclination movement or adduction movement is accomplished by bending the hand toward the cubital side of the forearm. The radial inclination movement or abduction movement is carried out by bending the hand toward the radial side. The sequence and combination of the above-described movements causes the circling motion. In contrast, the rotation of the hand is obtained by the movement of the hand about its own axis.

All of these movements are accomplished through the carpiradialis and carpimedian articulations and through the flexor and extensor muscles of the forearm and of the hand. These are innervated by the median nerve which crosses the carpal canal constituted by the rigid osseous sulcus of the carpal bones on which the traverse ligament is stretched.

The neuropathy to which the present invention is addressed arises from the unbalanced relationship between the cavity constituting the carpal canal and its sheath and the respective nerve, as well as from endogenous and exogenous factors which may cause such a degenerative process. The exogenous factors can include inflammatory processes, such as rheumatoid arthritis, fractures of the wrist and of the osseous corn, acromegaly (abnormal swelling of the bones), pregnancy etc.

From the repeated observations of patients affected by such pathology, it has been noted that a very frequent etiology is due to a particular exogenous factor. This exogenous factor is the frequent constrained position of the extension and bending of the wrist which can injure the median nerve caused by the increase of the pressure occuring in the carpal canal. Consequences of this pathology are irritative disorders, diffuse pain, paresthesia (tingling), as well as a further loss of the contractile strength of some of the muscles. This can lead to the atrophy of the muscles themselves. The most usual treatment for this pathology is of a conservative nature in which anti-inflammatory medications are used along the nerve. This treatment causes inconveniences and can even cause damage to the nerve. Often, the advantage obtained by such treatment processes is only temporary.

A first alternative to such anti-inflammatory medications is the use of wrist splints. These wrist splints utilize metal splints having a padding. These splints prevent hyperextensive movements and bending so as to relieve the suffering of the nerve. However, it is necessary to arrange the wrist-splint "ad hoc and in situ" by a technician. The use of such a splint can limit the activity of the wrists related to the daily and working activities of the patient. It also may be the impossible to remove by the patient.

On the same principle as that of the splints, other orthopedic remedies are proposed which basically utilize arm-bands worn by the patient with the purpose of limiting the sliding of the nerve along the carpal canal as much as possible. These remedies do not allow for the normal use of the hand. Their correct positioning is not always simple. Often, these remedies are not born by the patients for suitable periods of time necessary for the treatment of the carpal tunnel syndrome.

It is important to note that such remedies are sometimes used in an improper manner for carpal tunnel syndrome. It is fundamental that it is necessary to limit the bending/ extension of the wrist without blocking completely the movements of the wrist because the blocking of the wrist movement causes injury to the nerve. This is proven by the fact that carpal tunnel syndrome often arises after a wrist is fractured and plastered in place.

The present invention inventors were the inventors for Italian Patent Application Ser. No. FI/95/A/257 of Dec. 21, 1995 (otherwise identified as International Application No. PCT/IT96/00262 of Dec. 20, 1996). This patent application described a removable wrist band adjuvant for the treatment of carpal tunnel syndrome. This wrist band consisted of an armband for containing or preventing the bending movements, extension movements, radial and cubital inclination movements and movements of rotation of the carpi-radialis and carpiulnaris articulations of the wrist. This device allowed for the opposing of the thumb and the normal use of the hand. This armband, padded and countershaped according to the wrist and partially to the hand, is basically constituted by a shell having a rigid, but padded frame having two sides. The smaller of the sides is turned toward the forearm and the larger of the sides is turned toward the digits of the hand. This device presented an inconvenience in that, once the patient has worn the wrist-band, it did not remain in the desired position for therapeutic purposes, but would slide along the forearm. Additionally, this device offers a non-perfect containment of the wrist relative to the bending movements of the wrist.

It is an object of the present invention to prevent carpal tunnel syndrome without using pharmacological medications and by using a device which can be positioned directly by the patient without the help of a technician.

It is another object of the present invention to provide a wrist band for use by the patient which is compatible with the daily activities of the patient and which can be easily positioned and removed by the patient.

It is another object of the present invention to provide a wrist band which does not prevent the patient from carrying out his normal working activities and which does not block completely the hand causing the suffering of the median nerve.

It is another object of the present invention to provide a wrist band device which is easy and inexpensive to manufacture without using specialized workers and which is reproducible on an industrial scale without the use of sophisticated technologies and equipments.

It is a further object of the present invention to provide a wrist band device that can be manufactured in desired quantities.

BRIEF SUMMARY OF THE INVENTION

These objects of the present invention are achieved by a wrist band of the present invention for the prevention and the treatment of carpal tunnel syndrome. The wrist band is constituted by a soft and flexible multi-layer band suitable for being placed on a portion between the hand and the forearm corresponding to the carpiradialis articulation of the user. The band has five adjacent portions of which terminal first portion is coincident with the volar face of the wrist and has three rounded sides of which one is a terminal side and the other two extend therefrom. The other two sides are a superior side and an inferior side which are connected through respective surfaces to a second portion adjacent to the first terminal portion. The second portion is approximately coincident with the dorsal face of the wrist and includes two opposite sides. These two opposite sides includes a superior rounded side which is connected through a groove to the adjacent first portion and an inferior rectilinear side which is connected to a third portion adjacent to the second portion and overlapping the first portion. The third portion has two opposite sides of which one of the sides is a superior rounded side and the other is an inferior side which is a continuation of the inferior rectilinear side of the second portion. The third portion is connected to a fourth portion. The fourth portion is of a smaller size than the other portions. The fourth portion also has two opposite sides, a superior rounded side and an inferior rounded side. These superior and inferior rounded sides are connected through two further grooves to a fifth tongue-shaped terminal portion having three consecutive rounded sides. An internal face of the fifth portion has a fastening means thereon. The fastening means is a hook-and-loop material, commonly known as "VELCRO" (TM).

Further characteristics and advantages of the present invention will more clearly arise from the description of the preferred, but not exclusive embodiment, of the wrist band as illustrated in the attached drawings.

BRIEF DESCRIPTION OF THE SEVERAL VIEWS OF THE DRAWINGS

FIG. 1 shows a dorsal view of the open wrist-band.

FIG. 2 shows an internal view of the open wrist-band.

FIG. 3 shows a cross-sectional view of a central portion of the wrist band.

FIG. 4 shows a perspective view of the wrist band in its position as used.

FIG. 5 shows a perspective view of the wrist band of the present invention and, in particular, shows the positioning of the wrist within the wrist band.

DETAILED DESCRIPTION OF THE INVENTION

In FIGS. 1 and 2, there is shown a soft and flexible multi-layer band in an open position. This band is indicated by the reference numeral 10. In FIG. 1, the dorsal face 1 is shown. In FIG. 2, the internal face 11 is shown. The band 10 has a generally curved longitudinal axis X and is divided into five portions 2, 3, 4, 5 and 6. Portions 2, 3, 4, 5 and 6 are arranged so as to have respective transverse axis y2, y3, y4, y5 and y6 arranged in a fan-shaped manner. The first three portions 2, 3 and 4 are each adjacent to each other.

These three portions 2, 3 and 4 have respective superior rounded sides 12, 13 and 14. Sides 12 and 13 are connected along groove 22. Sides 13 and 14 are connected along groove 23. The inferior rounded side 32 of the first portion 2 is connected along the surface 33 to the rectilinear inferior side 31. This same arrangement occurs for portions 3 and 4. The side of the head of the portion 2 is also rounded and defines the ovoidal shape of this portion. The portion 4 is connected to the portion 5 along groove 24 and downward through groove 34. The portion 5, having rounded superior side 25 as well as inferior side 35, is connected through the superior groove 52 and the inferior groove 53 to the terminal portion 6. The terminal portion 6 is tongue-shaped and has a smaller size than the other portions.

The external face 1 has an area 20 between portions 3 and 4. Area 20 has a shape similar to that of tongue-shaped portion 6. Area 20 is suitable for the positioning of a fastening means when the band has been wrapped around the wrist in a manner similar to that of an armband.

The band 10, as shown in FIG. 3, includes a first external layer 7, a second internal layer 8 and a third external layer 9. The first external layer is of a soft and flexible material, such as leather, imitation leather or other washable and waterproof material. The second internal layer is of a gutta-percha or other flexible insulating material that is suitable for structurally connecting the first external layer 7 to the third external layer 9. The third external layer 9 is of a non-toxic, transpiring, washable textile material suitable for being in touch with the epidermis of the wrist. Three areas 15, 16 and 17 are approximately coincident with the portions 2, 3 and 4. In these areas 15, 16 and 17, between the second layer 8 and the third layer 9, are leather stiffening portions 29. These stiffening portions 29 have a thickness suitable for allowing them to be stiff for the containment of the wrist, but at the same time, being flexible for adapting to the anatomical morphology of the wrist. The stiffening portions 29 can be of a leather material or be of a plastic or an agglomerated natural fiber having the requisite mechanical characteristics and resistance for obtaining the same purpose as leather. A circular eyelet 21 is provided in the center of portion 3.

In FIG. 4, the configuration of the wrist band 30 is obtained by the folding of the band 10 about the areas 47, 48 and 49 of lesser resistance. As a result, the band 10 will have a tubular configuration adapted for the morphology of the wrist. The device 30 will have a first major opening 51 facing the digits of the hand and a smaller opening 52 facing the forearm of the user. The device is generally funnel-shaped.

In FIG. 5, the wrist band device 30 is shown as positioned on the wrist of a right hand. For the correct positioning, the posterior or dorsal face 26 of the hand will be turned upwardly. The lap 36 of the wrist band 30 has an edge 18 turned toward the fingers of the hand. Edge 18 corresponds to the side 13 of the portion 3. The edge 19, constituted by the side 31, is facing the forearm. The eyelet 21 is placed according to the protrusion 50 of the capital of the ulna. The lap 37 is positioned so as to be coincident with the front or palmar face of the hand. The edge 27 is turned toward the fingers and the opposite edge 28 is turned toward the forearm. In this manner, the band is tightly maintained during the successive step in which the lateral face 40 of the forearm will be leaned toward the thorax of the patient.

The lap 38 is passed under the lap 37 with a rotating movement toward the medial side of the forearm so as to exactly overlap itself to carry out, once the steps of positioning are finished, a consistent blockage of the bending movements of the wrist. As a result, the lap 39 will lie upon the lap 36 so as to close the eyelet 21 into which the protrusion 50 of the ulna has already been inserted. At this point, the next step will be to grasp the tongue-shaped edge 41 to carrying out the fixing of the wrist band upon the wrist. This is obtained through the overlapping of the fastening means 43 to the corresponding fastening means 45 on the external face of the lap 36.

The correct positioning of the wrist band is particularly relevant for achieving therapeutic purposes. The exact axial alignment of the lap 36 with the laps 37 and 38 will have to be in such a position to house the most developed raised area of the hand. This area will correspond to a thumb and is defined by the fleshy mass of the three muscles (i.e., the brief flexor of the thumb, the brief abductor of the thumb and the opponent of the thumb). The groove 44 is constituted by the folding of the wrist band in the area of smaller resistance 49. The raised area (known as ipothenar eminence) has an ovoidal elongated shape of with a larger pole turned toward the thumb and consequently countershaped to the aforementioned groove. On the opposite side, the groove 46 is constituted by the folding of the band in the area of smaller resistance 48. This groove 46 will be in a position so as to house the minor projecting raised area (known as ipothenar eminence) of elliptical elongate shape so as to correspond to the little finger of the hand. It is constituted by the abductor, the brief flexor and the opponent muscles of the little finger. The correct and stable positioning on the wrist is obtained when the eyelet 21 is coincident with the capital of the ulna (malleolus) 50. This will determine a fixed positioning and will avoid the possible excursions of the wrist band in both the transversal and longitudinal directions.

The advantages of such a wrist-band device are due to the immediate and easy positioning directly on the wrist with simple movements carried out directly by the patient. The present invention allows a range of adjustments and intermediate tightening which allows for easy adaptability of the wrist band to the different daily activities of the patient. The wrist band can be tightened when the wrist is at rest and loosened in the other cases.

The simple and pleasant shape of the wrist band device of the present invention makes it acceptable among most patients without distinction by sex or activities. The present invention allows a continuous, even prolonged use so as to allow for proper therapeutic time.

What is claimed is:

1. An apparatus for a wrist for the prevention and treatment of carpal tunnel syndrome which allows for a limited movement of the wrist, the wrist band comprising:
    a multi-layer soft and flexible band suitable for placement at a carpiulnaris articulation between a hand and a forearm of a user, said band comprising:
        a terminal first portion having three rounded sides, one of said sides being a terminal side, another of said sides being a superior side, another of said sides being an inferior side;
        a second portion connected to said first portion along a groove of said superior side and a surface of said interior side, said second portion having a superior rounded side and an inferior rectilinear side;
        a third portion connected adjacent said second portion and suitable for overlapping said first portion, said third portion having two opposite sides, one of said opposite sides being rounded, another of said opposite sides being a continuation of said inferior rectilinear side of said second portion;
        a fourth portion connected adjacent to said third portion, said fourth portion being of a size smaller than a size of any of said first portion and said second portion and said third portion, said fourth portion having a superior side and an inferior side opposite to each other; and
        a terminal tongue-shaped fifth portion having three consecutive rounded sides, said fifth portion having an internal face with a fastening means thereon, said fastening means being a hook-and-loop fastener.

2. The apparatus of claim 1, said band having a curved longitudinal axis, each of said portions having an axis transverse to said longitudinal axis, the axes extending in a fan-shaped manner.

3. The apparatus of claim 1, to said second and third portions having an external face with a fastening means thereon, said fastening means of said external face of said second and third portions being a hook-and-loop fastener complementary to said hook-and-loop fastener of said firth portion.

4. The apparatus of claim 1, said third portion having a circular eyelet formed in a center thereof.

5. The apparatus of claim 1, said band having three layers.

6. The apparatus of claim 5, one of said three layers being an external leather layer.

7. The apparatus of claim 5, one of said three layers being an washable and waterproof material.

8. The apparatus of claim 5, one of said three layers being an interior layer formed of a guttha-percha material.

9. The apparatus of claim 5, one of said three layers being an interior layer formed of a flexible and insulating material.

10. The apparatus of claim 5, one of said three layers being an exterior layer formed of a non-toxic, transpiring, washable textile material.

11. The apparatus of claim 5, said band having three stiffening portions between two of said three layers, said stiffening portions corresponding respectively to said first portion and said second portion and said third portion.

12. The apparatus of claim 11, said stiffening portions being of a leather material.

13. The apparatus of claim 11, said stiffening portions being of a plastic material.

14. The apparatus of claim 11, said stiffening portions being of a agglomerated natural fiber material.

15. The apparatus of claim 1, said first portion and said second portion of said third portion being foldable into a tubular and funnel-shaped configuration.

16. A method of using a wrist band to prevent and treat carpal tunnel syndrome of a hand, the wrist band having a first portion, a second portion, a third portion, a fourth portion, and a fifth portion, the method comprising:
    positioning the hand so as to have a dorsal face thereof turned upwards;
    placing the second portion of the band on said dorsal face such that a rounded side of the second portion facing toward fingers of the hand, the second portion having another side faces toward a forearm of the user, the second portion having an eyelet positioned over a protrusion of a capital of an ulna of the hand;
    lapping the band such that the first portion is positioned coincident with a palmar face of the hand, the first portion having a rounded side facing the fingers of the hand and an opposite side facing the forearm;
    leaning a lateral face of the forearm toward a thorax of the user so as to maintain the band in place;

lapping a third portion under the first portion in a circular movement towards a median side of the forearm so as to superimpose the first portion on the third portion;

overlapping the fourth portion onto the second portion so as to close the eyelet; and fastening a tongue-shaped edge of the band onto a surface of the band so as to fix the band in place on the hand.

17. The apparatus of claim 16 further comprising:

positioning an area between the second and third portion over a thener eminence of the hand; and positioning an area between the first and second portions over an ipothemar eminence of the hand.

\* \* \* \* \*